United States Patent [19]

O'Meara

[11] Patent Number: 5,042,690

[45] Date of Patent: Aug. 27, 1991

[54] UNIT DOSE ASSEMBLY

[75] Inventor: John R. O'Meara, Jamesburg, N.J.

[73] Assignee: CP Packaging, Inc., Jamesburg, N.J.

[21] Appl. No.: 476,689

[22] Filed: Feb. 8, 1990

[51] Int. Cl.$^5$ .............................................. B67D 5/00
[52] U.S. Cl. ....................................... 222/83; 222/187;
    222/541; 206/15.2; 401/134; 401/139; 401/267
[58] Field of Search ................ 222/83, 83.5, 107, 153,
    222/215, 541, 545, 570, 187, 522; 215/6, 250,
    257; 401/261, 267, 139, 134; 206/15.2

[56]  References Cited

U.S. PATENT DOCUMENTS

| | | | |
|---|---|---|---|
| 2,771,218 | 11/1956 | Henderson | 222/83 |
| 3,349,966 | 10/1967 | Schwartzman | 222/187 X |
| 3,414,360 | 12/1968 | Schwartzman | 401/134 |
| 3,454,196 | 7/1969 | Hazard | 222/541 X |
| 3,481,676 | 12/1969 | Schwartzman | 401/134 |
| 3,922,099 | 11/1975 | Christine et al. | 222/107 X |
| 4,271,982 | 6/1981 | Niksich | 401/134 X |
| 4,296,786 | 10/1981 | Brignola | 222/83.5 X |
| 4,456,150 | 6/1985 | Yang | 222/83 |
| 4,681,243 | 7/1987 | Takasugi | 222/83 |
| 4,723,687 | 2/1988 | Kutterer | 222/83 |
| 4,867,326 | 9/1989 | O'Meara | 222/83 X |
| 4,875,602 | 10/1989 | Chickering et al. | 222/187 |
| 4,884,703 | 12/1989 | O'Meara | 222/83 X |

FOREIGN PATENT DOCUMENTS

| | | | |
|---|---|---|---|
| 1961542 | 7/1971 | Fed. Rep. of Germany | 401/134 |
| 641359 | 2/1984 | Switzerland | 401/134 |

Primary Examiner—Michael S. Huppert
Assistant Examiner—Gregory L. Huson
Attorney, Agent, or Firm—Eugene E. Renz, Jr.

[57]  ABSTRACT

A cap and tube assembly device including a tube with a nozzle mounted on one end of the tube and having a thin wall section puncturable to provide a discharge on the other end of the nozzle. Also provided is a cap having a first end with an inside cross section sized to engage the nozzle and having an axially centered puncture spike positioned in a first position spaced from the thin wall and movable to a second position to puncture the thin wall. The puncture spike has a chisel shaped edge for forming a hole in the wall and a central bore for providing access to the contents of the tube. The cap has a second enclosing an applicator for dispensing the contents of the tube, whereby the contents of the tube is transferred to the applicator through the bore of the puncture means.

5 Claims, 1 Drawing Sheet

UNIT DOSE ASSEMBLY

FIELD OF THE INVENTION

This invention relates to a unit dose assembly and more particularly to a cap for use with a tube in which a unit dose is provided in the tube. The tube may contain a single dose of medicine, eyewash, disinfectant or other pharmaceutically related product. The device is particularly suitable for use with medicaments which need to be topically applied, and is ideal for use with iodine solutions which are used to sterilize and clean skin prior to injections or I-V insertions.

BACKGROUND OF THE INVENTION

Cape and tube assemblies which carry medicines and the like have obtained significant interest in the pharmaceutical industry. Not only is there a concern for resistance to undesirable tampering, such as by a child, there is increased interest in application of sterile fluids to the body for various treatment purposes.

In my recent patent, U.S. Pat. No. 4,867,326, I have provided an excellent design for a child resistant cap. The design described in my patent is of great value in providing a product wherein there is easy and convenient inspection of unit dose sterile medicaments in a cap and tube assembly. The unit is child resistant and suitable for a high reliability pass/fail inspection by the user.

In my patented design, the cap is used to activate or pierce a thin wall in the tube which provides access to the contents of the tube. The cap then must be removed and the contents may be deployed. While this system is excellent for delivering unit doses of medicines, such as, for example, eyedrops, the prior art designs have not been entirely satisfactory when the contents of the tube are to be applied topically. Accordingly, one object of the present invention is to provide a unit dose assembly for topical applications of the contents.

Often times, it is particularly desirable to be able to apply disinfectant and other sterilizing solutions to the skin directly, such as when injections or incisions are being made. Iodine solutions are often rubbed on the skin prior to administration of an injection.

Even in surgery, there are times when it is desirable to apply disinfectants or other medicaments topically. In operating room conditions, it is absolutely essential that the equipment be sterile and be protected from contamination from exterior sources. Thus, while the contents of a container might be sterile and suitable for use in surgery or other operating room procedures, the outside of the container itself is not sterile.

Additionally, even when a particular solution is used repetitively in a surgical procedure, it is less than desirable to have large quantities of these solutions. If all of the solution is not used, it is either wasted by being discarded or it represents a potential source of contamination when it is used during a succeeding procedure. For that reason, sterile unit dose applications of these solutions would be of great advantage to the art. It is another object of this invention to provide unit dose assemblies for topical applications under sterile conditions such as operating room environments.

One particular concern in surgical facilities is the need to account for objects before and after surgery. Accordingly, if a unit dose system were to be provided which would be sterile and otherwise suitable for accomplishing the objects of the present invention, concern would always remain that the cap might be lost. Once it has been used to puncture the thin wall end of the tube and has been removed to permit access to the contents of the tube, it must be accounted for separately. Accordingly, it is an object of this invention to provide a unit dose assembly for topical applications which remains in one piece after access to the tube has been obtained.

Other objects will appear hereinafter.

SUMMARY OF THE INVENTION

It has now been discovered that the above and other objects of the present invention may be accomplished in the following manner. Specifically, a cap for a unit dose assembly for topical application has been discovered which includes the following components.

A tube containing a unit dose, such as a quantity of iodine for sterilizing or cleaning the skin, is provided with a nozzle having one end mounted on or part of one end of the tube and a thin end wall section on the other end of the nozzle. The thin wall section is puncturable to provide a discharge of the contents. A major part of the assembly is a cap having a first end with an inside cross section sized to engage the nozzle, the cap has an axially centered puncture means positioned to puncture the thin wall when it is moved from a first position spaced therefrom, during storage, to a second position during use. The puncture means includes a central bore for providing access to the contents of the tube. The cap includes a second end in communication with the first end through that central bore. The second end encloses an applicator for dispensing the contents of the tube, which may be accomplished when the thin wall or membrane is pierced by the puncture means.

In a preferred embodiment, the nozzle and first end of the cap have a ring and groove assembly or other arrangement by which a surface of resistance and an interference surface mutually combine to locate the cap with respect to the tube in the first position.

In another embodiment, the applicator means includes a material capable of expanding when fluid is transferred from the tube to the applicator. A preferred material is polyurethane since it can be sterilized, is soft, contains no threads and is Federal Drug Administration approved. Cotton, paper, other wicking materials, felt, sponges and other synthetic foams which have most of these same properties are also useful as applicator materials. In a preferred embodiment, the applicator and the second end include a means for preventing removal of the applicator during use.

The entire device is intended to be sterilized. The sterile package may be included in a blister pack which can be opened without contacting the sterile inside, for example, and dropped onto a sterile cloth in an operating room. Alternatively, a removable cover means may be placed on the second end, such as a peel off cover, to protect the applicator from contamination.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 1:
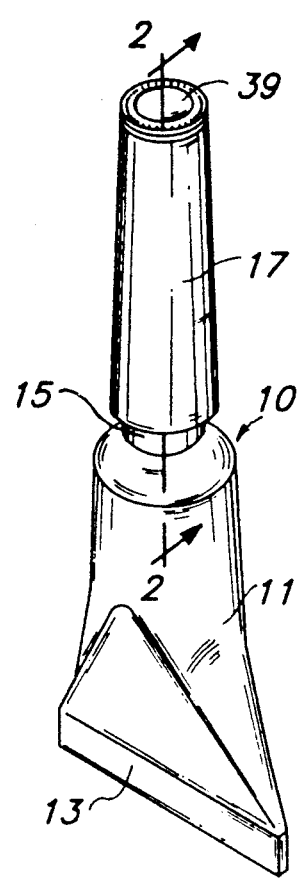
FIG. 1 is a perspective view of a tubular plastic unit dose assembly device of the present invention, showing a closed terminal end and a cap on the other end of the tube.

As shown in the figures, a unit dose assembly for topical applications shown generally by the reference numeral 10 includes a tube portion 11 which is sealed at one end 13 after a quantity of medicament has been placed inside the tube 11. The tube 11 has a nozzle 15 at the other end, and the nozzle 15 is fitted with a cap 17.

Figure 2:
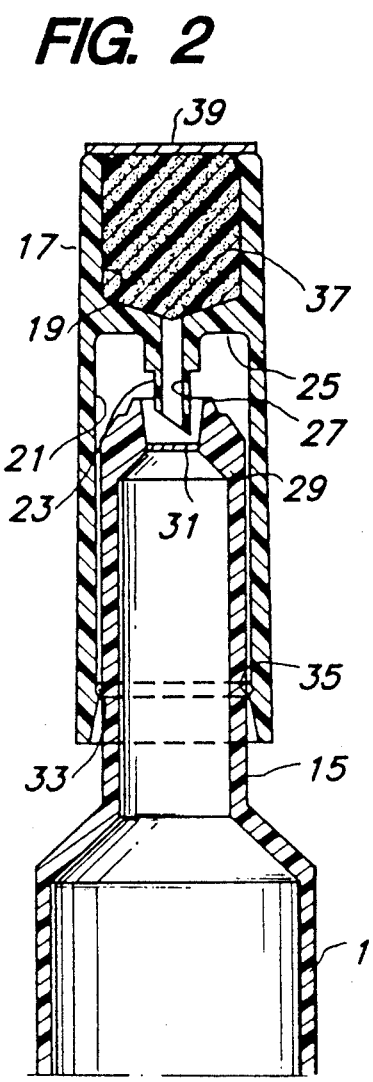
FIG. 2 is an enlarged, fragmentary sectional elevational view taken along the line 2,2 of FIG. 1.

As shown in FIG. 2, the cap 17 has an upper compartment 19 and lower compartment 21. The lower compartment 21 includes a piercing means 23 which is supported by the divider disc 25. Divider disc 25 separates the upper compartment 19 and the lower compartment 21. The piercer 23 includes an orifice 27 through the piercer 23, which permits transfer of the contents of the tube 11 from the lower compartment 21 to the upper compartment 19.

The nozzle 15 is joined at one end to the tube 11 and at the other end is provided with a nozzle tip 29. Nozzle tip 29 includes a thin wall portion 31, which is of sufficient thickness to prevent the contents of the tube 11 from being removed until the membrane 31 is penetrated.

The cap 17 is located in a first position on the nozzle 15 by a groove 33 and ring 35. This combination of ring and groove provides a surface of resistance in the groove and an interference surface in the ring. Of course, the ring 35 can be placed on the cap 17 and the groove on the nozzle 15 if desired.

The upper portion 19 of the cap 17 is preferably filled with a material which is suitable for use as an applicator. Polyurethane foam and other synthetic foam materials, felt, sponges, paper and other wicking materials, cotton, and other soft materials can be used, depending upon the material contained in the tube and the use for which it is intended. It is preferred to use a polyurethane foam, or something similar, which can be sterilized, such as by gamma radiation, and which is soft, has no threads, and is FDA approved.

In order to activate the device of the present invention, all that is necessary is to press on the upper compartment 19 of the cap 17 so that the piercing member 23 penetrates the thin membrane 31. The force needs to be sufficient to overcome the resistance due to the groove 33 and ring 35.

Figure 3:
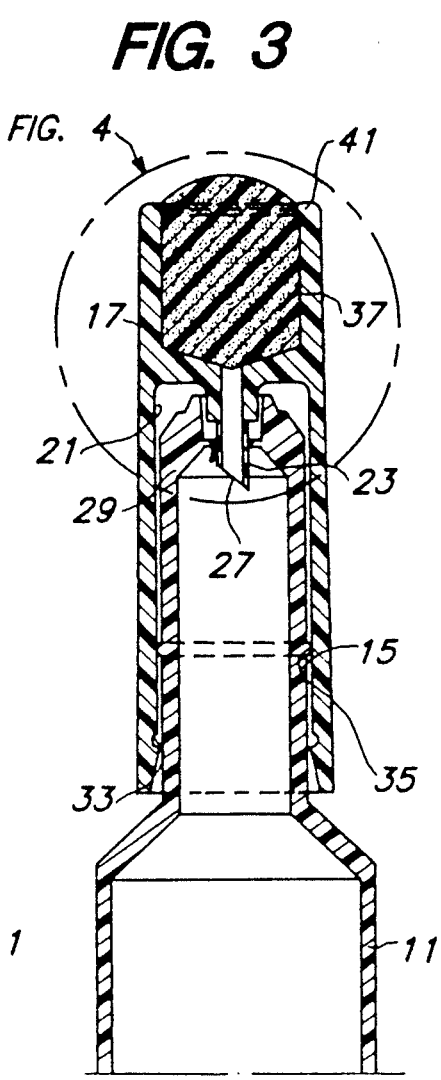
FIG. 3 is a view similar to that to FIG. 2, but showing the outer cap member moved forcefully downward, upon the neck portion of the tube, driving the piercing point through the thin wall, creating an opening by which the medicament may be dispensed.

As seen in FIG. 3, the lower chamber 21 of the cap 17 now fully accommodates the nozzle 15. The piercing member 23 extends into the nozzle 15 and beyond the nozzle tip 29. Contents contained in tube 11 may now pass through the orifice or hole 27 in the piercer 23 and contact the applicator material 37.

Typically, when a liquid is contained in the tube 11, and the tube 11 is squeezed or otherwise caused to force liquid to flow through the hole 27, the applicator material 37 will expand slightly due to its being filled with the fluid.

Figure 4:
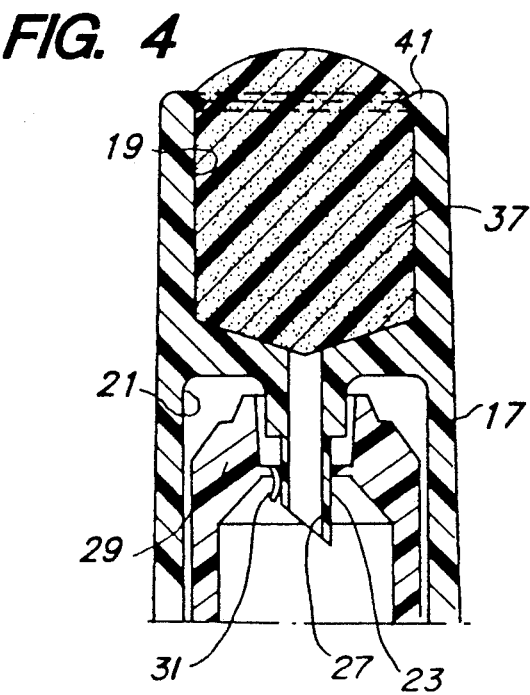
FIG. 4 is a greatly enlarged view of the detail contained within the dot and dash circle of FIG. 3 and designated FIG. 4, showing the details of the applicator portion of the design.

As shown in FIG. 4, a liquid has entered the urethane foam 37 and extends out beyond the end of the upper compartment 19. This expansion of the foam 37 can also take place in the dry form, prior to puncturing the thin wall membrane 31. For example, an optional cover 39 shown in FIG. 2, can maintain the applicator material 37 under compression until it is removed and the system is activated. Then, the applicator material 37 will expand as shown in FIGS. 3 and 4.

It is recognized that use of the device of this invention requires that the contents of the tube 11 be forced through the hole 27. This transfer of contents will put some pressure on the applicator material 37. Particularly if the tube is squeezed excessively, the applicator material 37 may not accommodate the fluid as rapidly as is desired. In order to preserve the integrity of the device and prevent the applicator material 37 from escaping from the upper compartment 19, a shoulder 41 is formed in the upper compartment 19 and this shoulder 41 prevents movement of the applicator material 37.

In an alternative embodiment, the applicator material 37 can be bonded, by heat or adhesive for example, to the dividing wall 25 separating the upper compartment 19 from the rest of the cap 17. Care should obviously be exercised to prevent plugging the hole 27 and no adhesive materials which are not fully approved by the FDA and other agencies should be employed.

Figure 5:
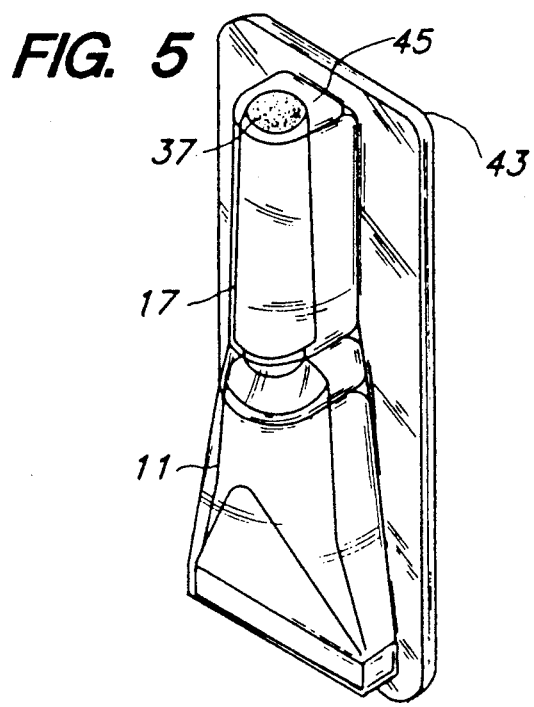
FIG. 5 is a perspective view of a preferred embodiment of this invention, shown in a package.

Instead of employing a cover such as the tab 39 shown in FIG. 2, it is contemplated that a preferred embodiment of the present invention will incorporate the device in a package, such as a flexible, sterilizable envelope. As shown in FIG. 5, the tube 11, cap 17 and exposed applicator material 37 are positioned on a substrate 43 which forms an envelope 45 using conventional technology. Instructions and advertisements can be printed on either the substrate or the blister pack as desired. The packaging can be a paper-mylar envelope or a blister pack or other packing which can be sterilized by steam, gamma radiation and the like.

It is intended that the device of the present invention will be sterilized prior to use. While there are a variety of ways for sterilizing, such as might be employed in the assembly of the device in its marketable form, it is preferred that the device be assembled and thereafter be sterilized using gamma ray sterilization techniques. Unless the contents of the tube 11 are sensitive to gamma ray sterilization, this is the most effective way to ensure that the entire device is sterile.

Since one of the preferred uses for the present invention is to dispense iodine solutions which themselves are used to sterilize and clean skin prior to injection or other surgical procedures, it is contemplated that these devices will be used in an operating room facility. In the blister pack embodiment, the device has been sterilized and is maintained sterile until it is time for use. Although the exterior envelope 45 and the substrate 43 may be contaminated, however slightly, by the environment, it is contemplated that someone in the operating room will be directly responsible for opening the package and allowing the tube 11 and cap 17 assembly to be removed and placed on a sterile tray without the tube assembly 11 being touched. This is often done by a perimeter nurse. The surgeons and assistants who have been sterilized and are wearing sterilized gloves will then pick up the tube 11 in a sterile condition and will not have had to have contacted the outside of a tube that could have been contaminated in any way.

Because of the present design, the cap 17 is not removed from the tube 11. For this reason, operating room parts counting procedures are not confused when the present invention is used.

While particular embodiments of the invention have been illustrated and described herein, it is not intended to limit the invention. Changes and modifications may be made herein within the scope of the following claims.

What is claimed is:

1. A cap and tube assembly device comprising:
   a tube for containing a product and having a nozzle mounted on one end of said tube, with a thin wall section puncturable to provide a discharge;
   a cap having a first end with an inside cross section sized to engage said nozzle and having an axially centered sharp, pointed, hollow puncture means positioned in a first position spaced from said thin wall and movable to a second position to puncture said thin wall;
   wherein the outside of said nozzle is provided with a surface of resistance and the inside of said first end of said cap has an interference surface, said surface of resistance and interference surface comprising a ring and groove whereby said surface of resistance and said interference surface cooperate to locate said puncture means in said first position;
   said puncture means having a central bore for puncturing said thin wall to provide access to the contents and of said tube; and
   said cap having a second end in communication with said first end via said bore and including means for fixedly enclosing and retaining an applicator for dispensing the contents of said tube, said applicator comprising a material capable of expanding when fluid is transferred from said tube to said applicator.

2. The device of claim 1 wherein said assembly is sterilized.

3. The device of claim 1 wherein said material is polyurethane foam.

4. The device of claim 3 wherein said assembly is packaged.

5. The device of claim 3 which further includes a removable cover means on said second end to protect said applicator from contamination.

* * * * *